(12) United States Patent
Lee et al.

(10) Patent No.: US 9,657,264 B2
(45) Date of Patent: May 23, 2017

(54) MICROORGANISMS FOR PRODUCING PUTRESCINE AND PROCESS FOR PRODUCING PUTRESCINE USING THEM

(71) Applicant: CJ CHEILJEDANG CORPORATION, Seoul (KR)

(72) Inventors: Kyoung Min Lee, Seoul (KR); Hongxian Li, Seoul (KR); Su Jin Park, Seoul (KR); Young Lyeol Yang, Seoul (KR); Hye Won Um, Gyeonggi-do (KR); Hee Kyoung Jung, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/306,753

(22) PCT Filed: Apr. 24, 2015

(86) PCT No.: PCT/KR2015/004087
§ 371 (c)(1),
(2) Date: Oct. 25, 2016

(87) PCT Pub. No.: WO2015/163718
PCT Pub. Date: Oct. 29, 2015

(65) Prior Publication Data
US 2017/0044487 A1    Feb. 16, 2017

(30) Foreign Application Priority Data

Apr. 25, 2014 (KR) .................. 10-2014-0049766

(51) Int. Cl.
*C12N 1/20* (2006.01)
*C12P 13/00* (2006.01)

(52) U.S. Cl.
CPC ............. *C12N 1/20* (2013.01); *C12P 13/001* (2013.01)

(58) Field of Classification Search
CPC .......... C12P 13/00; C07K 14/34; A61K 38/00
USPC .............................................. 435/128, 252.2
See application file for complete search history.

(56) References Cited

FOREIGN PATENT DOCUMENTS

| KR | 1020120064046 A | 6/2012 |
| KR | 1020130082478 A | 7/2013 |
| KR | 1020130086010 A | 7/2013 |
| KR | 1013484610000 A | 12/2013 |
| WO | 2006/005603 A2 | 1/2006 |
| WO | 2009/125924 A2 | 10/2009 |

OTHER PUBLICATIONS

Blombach et al., "L-Valine Production during Growth of Pyruvate Dehydrogenase Complex-Deficient Corynebacterium glutamicum in the Presence of Ethanol or by Inactivation of the Transcriptional Regulator SugR," Applied and Environmental Microbiology 75(4): 1197-1200, Feb. 2009.
Igarashi and Kashiwagi, "Characteristics of cellular polyamine transport in prokaryotes and eukaryotes," Plant Physiology and Biochemistry 48: 506-512, 2010.
Itou et al., "The CGL2612 Protein from Corynebacterium glutamicum is a Drug Resistance-related Transcriptional Repressor. Structural and Functional Analysis of a Newly Identified Transcription Factor From Genomic DNA Analysis," The Journal of Biological Chemistry 280(46): 38711-38719, Nov. 18, 2005.
Nakamura et al., "Mutations of the Corynebacterium glutamicum NCgl1221 Gene, Encoding a Mechanosensitive Channel Homolog, Induce L-Glutamic Acid Production," Applied and Environmental Microbiology 73(14): 4491-4498, Jul. 2007.
NCBI Reference Sequence: WP_011015249.1, "TetR family transcriptional regulator [Corynebacterium glutamicum]," Jul. 18, 2013.
Qian et al., "Metabolic Engineering of *Escherichia coli* for the Production of Putrescine: A Four Carbon Diamine," Biotechnology and Bioengineering 104: 651-662, 2009.
Schneider et al., "Improving putrescine production by Corynebacterium glutamicum by fine-tuning ornithine transcarbamoylase activity using a plasmid addiction system," Appl. Microbiol. Biotechnol. 95: 169-178, 2012.
Schneider and Wendisch, "Putrescine production by engineered Corynebacterium glutamicum," Appl. Microbiol. Biotechnol. 88: 859-868, 2010.

*Primary Examiner* — Tekchand Saidha

(57) ABSTRACT

The present invention relates to a recombinant microorganism capable of producing putrescine at high yield due to inactivated activity of a protein having an amino acid sequence represented by SEQ ID NO: 2 in the microorganism, and a method of producing putrescine using the microorganism.

8 Claims, 1 Drawing Sheet

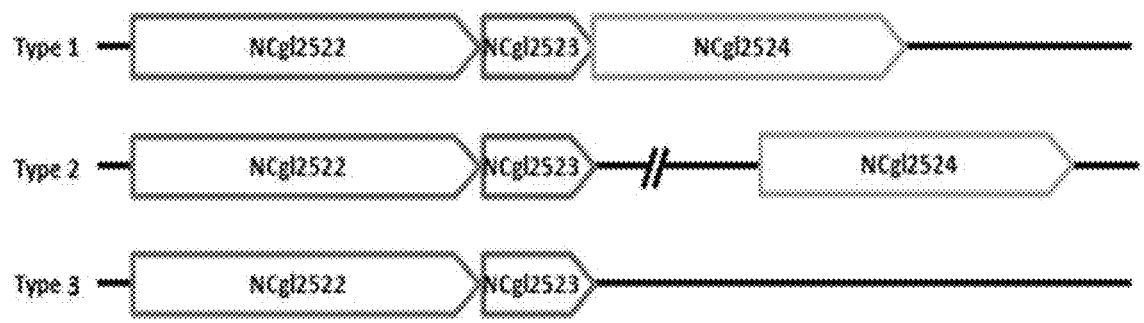

MICROORGANISMS FOR PRODUCING PUTRESCINE AND PROCESS FOR PRODUCING PUTRESCINE USING THEM

CROSS-REFERENCES TO RELATED APPLICATIONS

This application is a U.S. national phase application of International PCT Patent Application No. PCT/KR2015/004087, which was filed on Apr. 24, 2015, which claims priority to Korean Patent Application Nos. 10-2014-0049766, filed Apr. 25, 2014. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_049_00US_ST25.txt. The text file is 35 KB, was created on Oct. 25, 2016, and is being submitted electronically via EFS-Web.

TECHNICAL FIELD

The present invention relates to a recombinant microorganism for producing putrescine and a method of producing putrescine using the same.

BACKGROUND ART

Biogenic amines (BAs) are nitrogen compounds mainly produced by decarboxylation of amino acids, amination of aldehyde and ketone, and transamination. Such biogenic amines are low molecular weight compounds, which are synthesized during metabolism of microorganisms, plants, and animals, and thus are known as components easily found in cells thereof. Especially, polyamine such as spermidine, spermine, putrescine (or 1,4-butanediamine), cadaverine, etc., are substances present in most living cells.

Among them, putrescine is an important raw material which synthesizes polyamine nylon-4,6 by reacting with adipic acid, and is produced mainly by chemical synthesis through acrylonitrile and succinonitrile from propylene.

In addition, a method for producing putrescine at high concentration by transformation of *E. coli* and genus *Corynebacterium* has been disclosed (International Publication No. WO06/005603; International Publication No. WO09/125924; Qian Z D et al., Biotechnol. Bioeng. 104(4): 651-662, 2009; Schneider et al., Appl. Microbiol. Biotechnol. 88(4): 859-868, 2010; and Schneider et al., Appl. Microbiol. Biotechnol. 95: 169-178, 2012). Further, research on putrescine transporter regarding *E. coli*, yeast, plant and animal cells has been actively conducted (K Igarashi, Plant Physiol. Biochem. 48: 506-512, 2010).

Meanwhile, the present inventors demonstrated that membrane proteins encoding NCgl2522 function as a putrescine exporter in a microorganism of genus *Corynebacterium*, which includes a putrescine synthesis pathway, and confirmed that putrescine may be produced at a high yield by enhancing NCgl2522 activity from to the endogenous activity thereof (KR Patent Application No. 10-2013-0030020)

In addition, NCgl2523 gene is a multidrug-resistance-related transcription factor which belongs to TetR family, and is known to act as an NCgl2522 expression inhibitor (Hirochi et. al. J Biol. Chem. 280:46, 38711-38719. 2005).

In this regard, the present inventors have continuously conducted research and confirmed enhanced putrescine production by depletion of NCgl2523 which constitutes NCgl2522 operon, in the manner similar to the effects of enhancing NCgl2522 activity, thereby completing the present invention.

DISCLOSURE

Technical Problem

An objective of the present invention is to provide a recombinant microorganism capable of producing putrescine at high yield.

Another objective of the present invention is to provide a method of producing putrescine at high yield using the microorganism.

Technical Solution

In one aspect to achieve the above objectives, the present invention provides a microorganism of genus *Corynebacterium* having putrescine productivity, in which a protein having an amino acid sequence represented by SEQ ID NO: 2 is inactivated In one exemplary embodiment, the present invention provides a microorganism of genus *Corynebacterium* having putrescine productivity, wherein an activity of ornithine decarboxylase (ODC) is further introduced into the microorganism.

In another exemplary embodiment, the present invention provides a microorganism of genus *Corynebacterium* having putrescine productivity, in which the ODC has an amino acid sequence represented by SEQ ID NO: 10.

In still another exemplary embodiment, the present invention provides a microorganism of genus *Corynebacterium* having putrescine productivity, wherein acetyltransferase activity is further inactivated in the microorganism.

In still another embodiment, the present invention provides a microorganism of genus *Corynebacterium* having putrescine productivity, wherein the acetyltransferase comprises an amino acid represented by SEQ ID NO: 15 or 16.

In still another embodiment, the present invention provides a microorganism of genus *Corynebacterium* having putrescine productivity, in which the microorganism is *Corynebacterium glutamicum*.

In another aspect, the present invention provides a method of producing putrescine including:

i) culturing a microorganism of genus *Corynebacterium* having putrescine productivity wherein a protein having an amino acid sequence represented by SEQ ID NO: 2 is inactivated in a culture medium; and ii) separating putrescine from a cultured microorganism or the culture medium obtained from the above step.

In an exemplary embodiment, the present invention provides a method of producing putrescine, in which the microorganism of genus *Corynebacterium* is *Corynebacterium glutamicum*.

Hereinafter, the present invention will be described in detail.

In one aspect, the present invention relates to a microorganism of genus *Corynebacterium* having putrescine productivity, wherein a protein having an amino acid sequence represented by SEQ ID NO: 2, thus NCgl2523, is inactivated As used herein, the term "NCgl2523" refers to a multi-drug-resistance-related transcription factor which belongs to TetR family, and is known to act as an Ncgl2522 expression inhibitor (Hirochi et. al., J Biol. Chem. 280(46): 38711-38719, 2005).

In the present invention, NCgl2523 is a protein having an amino acid of SEQ ID NO: 2 or an amino acid sequence having 70% or more, more specifically 80% or more, even more specifically 90% or more, much more specifically 98% or more, and most specifically 99% or more homology to the sequence, and is not limited thereto as long as it is a protein having the activity of an NCgl2522 expression inhibitor.

Further, because amino acid sequences of proteins showing the activity may differ depending on species or strain of microorganisms, it is not limited thereto. It is obvious that a protein having an amino acid sequence in which the sequence is partially deleted, modified, substituted, or inserted is included in the scope of the present invention, as long as a sequence having homology to the sequence shows biological activity practically equivalent or corresponding to a protein of SEQ ID NO: 2.

As used herein, the term "homology" refers to similarity between given amino acid sequences or nucleotide sequences and may be represented in percentage. Herein, the homology sequence which have identical or similar activity with a given amino acid sequence or nucleotide sequence is indicated by "% homology". For example, homology may be examined by using conventional software calculating mediated parameters such as score, identity, similarity, etc., and more specifically using BLAST 2.0, or by comparing sequences via Southern hybridization under defined stringent conditions. Appropriate hybridization conditions may be defined by the scope of the art, and may be determined by one of ordinary skill in the art using known methods (i.e., J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York).

As long as it has an activity similar to those of NCgl2523 proteins, a polynucleotide encoding NCgl2523 of the present invention may include an amino acid sequence of SEQ ID NO: 2, or a polynucleotide encoding a protein having 70% or more, specifically 80% or more, more specifically 90% or more, much more specifically 95% or more homology thereto, much more specifically 98% or more, and most specifically 99% or more homology to the sequence, and may especially include a nucleotide sequence of SEQ ID NO: 1 or 3.

Further, a polynucleotide encoding NCgl2523 of the present invention may be hybridized in stringent conditions with a probe of a nucleotide sequence represented by SEQ ID NO: 1 or 3, or a probe derived from the nucleotide sequence, and may be a variant encoding functionally normal NCgl2523. As used herein, the term "stringent conditions" refers to conditions which enable a specific hybridization between polynucleotides. For example, such stringent conditions are described in detail in literature (i.e., J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York).

In the present invention, it was confirmed that when NCgl2523, which constitutes an NCgl2522 operon, was deleted in a microorganism of genus *Corynebacterium* having putrescine productivity, putrescine production increased, similarly to when NCgl2522 activity was enhanced. In this regard, the present invention may provide a recombinant microorganism showing putrescine production at a high yield by inhibiting NCgl2522 expression resulting from inactivating NCgl2523 activity. Therefore, as disclosed in the embodiment of the present invention, by inactivating the corresponding NCgl2523 and genes encoding amino acids similar thereto, putrescine productivity may be enhanced in a microorganism having amino acids having sequences similar to that of NCgl2523, in which such amino acids consist of NCgl2522 and an operon, or a microorganism in which NCgl2523 acts similarly as an NCgl2522 expression modulator.

As used herein, the term "inactivation" refers to not expressing a gene encoding a corresponding polypeptide, showing a certain reduction in gene expression, not producing a corresponding functional polypeptide, even when expressed.

In addition, inactivation refers not only to completely inactivating a gene encoding a corresponding polypeptide, but also to a weakened or significantly reduced expression compared to the wild-type, thereby practically not expressing the gene. Therefore, gene inactivation may be complete (knockout) or partial (for example, a hypomorph which shows gene expression below the normal level, or a product of a mutant gene which shows partial reduction in activity in effect of a hymorph).

In particular, in the present invention, inactivation of NCgl2523 may be induced by:
1) a partial or complete deletion of a polynucleotide encoding the protein;
2) modification of a regulatory sequence to decrease an expression of the polynucleotide;
3) modification of the polynucleotide sequence on chromosome in order to weaken the protein activity; and
4) a combination thereof,
without being particularly limited thereto.

1) a partial or complete deletion of a polynucleotide encoding the protein may be performed by replacing a polynucleotide encoding endogenous target proteins or chromosomes with a partially removed polynucleotide or a marker gene using a vector for chromosomal insertion into a microorganism. The "partial" may vary depending on the type of polynucleotides, but specifically refers to 1 to 300, more specifically to 1 to 100, and even more specifically 1 to 50.

As used herein, the term "vector" refers to a DNA construct including a nucleotide sequence encoding a desired protein, which is operably linked to an appropriate expression regulatory sequence to express the desired protein in a suitable host cell. The regulatory sequence includes a promoter that can initiate transcription, an optional operator sequence for regulating the transcription, a sequence encoding a suitable mRNA ribosome-binding site, and a sequence regulating the termination of transcription and translation. After the vector is transformed into a suitable host cell, it can replicate or function independently of the host genome, and can be integrated into the genome itself.

The vector used in the present invention is not particularly limited, as long as it is able to replicate in host cells, and any vector known in the art may be used. Examples of conventional vectors may include a natural or recombinant plasmid, cosmid, virus, and bacteriophage. For example, pWE15, M13, MBL3, MBL4, IXII, ASHII, APII, t10, t11, Charon4A, Charon21A, etc., may be used as a phage vector or cosmid vector, and pBR types, pUC types, pBluescriptII types, pGEM types, pTZ types, pCL types, pET types, etc., may be used as a plasmid vector. A vector usable in the present invention is not particularly limited, and any known expression vector may be used. Specifically, pDZ, pACYC177, pACYC184, pCL, pECCG117, pUC19, pBR322, pMW118, or pCC1BAC vector may be used.

Further, the polynucleotide encoding a desired protein in chromosomes may be replaced by a mutated polynucleotide using a vector for chromosomal insertion. The insertion of the polynucleotide into the chromosome may be performed by any method known in the art such as homologous recombination, without being particularly limited thereto.

As used herein, the term "transformation" refers to introduction of vectors including a polynucleotide encoding target proteins into host cells so that proteins encoded by the polynucleotide are expressed in host cells. As long as the transformed polynucleotide can be expressed in a host cell, it includes all whether it is integrated into chromosomes of host cells or exists extrachromosomally. Further, the polynucleotide includes DNA and RNA encoding target proteins. The polynucleotide may be introduced in any form, as long as it can be introduced into host cells and expressed therein. For example, the polynucleotide may be introduced into host cells in the form of an expression cassette which is a gene construct including all elements required for its autonomous expression. Typically, the expression cassette includes a promoter operably linked to the polynucleotide, transcriptional termination signals, ribosome-binding sites, or translation termination signals. The expression cassette may be in the form of a self-replicable expression vector. Also, the polynucleotide may be introduced into host cells as it is and operably linked to sequences required for expression in host cells, without being limited thereto.

Further, the term "operably linked" refers to a functional linkage between a polynucleotide sequence encoding desired proteins and a promoter sequence which initiates and mediates transcription of the polynucleotide sequence.

Next, 2) modification of a regulatory sequence to decrease an expression of the polynucleotide may be performed by inducing modification in a regulatory sequence by deletion, insertion, non-conservative or conservative substitution, or a combination thereof in a nucleotide sequence or replacing with a nucleotide with a weaker activity, in order to weaken the activity of the regulatory sequence, without being particularly limited thereto. The regulatory sequence may include a promoter, an operator sequence, a sequence encoding ribosome-binding site, and a sequence regulating termination of transcription and translation, without being limited thereto.

Further, 3) modification of the polynucleotide sequence on chromosome may be performed by inducing modification in a regulatory sequence deletion, insertion, non-conservative or conservative substitution, or a combination thereof in a nucleotide sequence, or replacing with a nucleotide with a weaker activity, in order to weaken the protein activity, without being limited thereto, As used herein, the term "a microorganism having putrescine productivity" or "a microorganism producing putrescine" refers to a microorganism naturally having putrescine productivity or a microorganism, in which putrescine productivity is incorporated into a parent strain having no putrescine productivity.

The microorganism producing putrescine may be, without being particularly limited thereto, a microorganism having improved productivity of ornithine to be used as a raw material for putrescine biosynthesis, in which the microorganism is modified to have higher activities of acetylglutamate synthase converting glutamate to acetylglutamate (N-acetylglutamate) or ornithine acetyltransferase (ArgJ) converting acetyl ornithine to ornithine, acetylglutamate kinase (ArgB) converting acetyl glutamate to acetylglutamyl phosphate (N-acetylglutamyl phosphate), acetyl-gamma-glutamyl phosphate reductase (ArgC) converting acetyl glutamyl phosphate to acetyl glutamate semialdehyde (N-acetyl glutamate semialdehyde), or acetylornithine aminotransferase (ArgD) converting acetyl glutamate semialdehyde to acetylornithine (N-acetylornithine), compared to the endogenous activity, in order to enhance the biosynthesis pathway from glutamate to ornithine glutamate.

Further, the microorganism is modified to inactivate endogenous activity of ornithine carbamoyltransfrase (ArgF) involved in arginine synthesis from ornithine, glutamate exporter (NCgl1221), and/or acetyltransferase which acetylizes putrescine and/or is modified to introduce activity of ornithine decarboxylase (ODC).

Here, the ornithine carbamoyltransfrase (ArgF), glutamate exporter (NCgl1221), ornithine decarboxylase (ODC), acetyl-gamma-glutamyl-phosphate reductase (ArgC), acetyl glutamate synthase or ornithineacetyltransferase (ArgJ), acetylglutamate kinase (ArgB), and acetylornithine aminotransferase (ArgD), may include specifically an amino acid sequence each represented by SEQ ID NO: 8, 9, 10, 11, 12, 13, and 14 or an amino acid sequence having 70% or more, more specifically 80% or more, even more specifically 90% or more homology to the sequence, without being particularly limited thereto.

Further, an acetyltransferase, which acetylizes putrescine, may include specifically an amino acid sequence represented by SEQ ID NO: 15 or 16 or an amino acid sequence having 70% or more, more specifically 80% or more, even more specifically 90% or more homology to the sequence, without being particularly limited thereto.

In particular, an increase in activity in the present invention may be carried out by:

1) an increase in the copy number of polynucleotides encoding the enzyme;

2) modification of a regulatory sequence to increase the polynucleotide expression;

3) modification of a polynucleotide sequence on chromosome to enhance activity of the enzyme; or 4) modification to enhance by a combination thereof, without being limited thereto.

1) an increase in the copy number of polynucleotides may be performed in the form operably liked to a vector, or by chromosomal insertion into host cells, without being particularly limited thereto. In particular, it may be performed by introducing a vector, to which a polynucleotide encoding an enzyme of the present invention enzyme operably linked and which may be copied and function independently of host cells into host cells, or by introducing a vector to which the polynucleotide is operably linked and which is able to insert the polynucleotide into choromosomes in host cells into host cells, thereby increasing the copy number of polynucleotides in chromosomes of the host cells.

Next, 2) modification of a regulatory sequence to increase the polynucleotide expression may be performed by inducing modification in a sequence by deletion, insertion, non-conservative or conservative substitution or a combination thereof, or replacing with a nucleotide sequence with enhanced activity, in order to enhance the activity the regulatory sequence, without being particularly limited thereto. The regulatory sequence may include a promoter, an operator sequence, a sequence encoding a ribosome-binding site, a sequence regulating termination of transcription and translation, etc., without being particularly limited thereto.

In the upstream of the polynucleotide expression unit, a strong heterologous promoter may be linked instead of the original promoter. Examples of the strong promoter are CJ7 promoter, lysCP1 promoter, EF-Tu promoter, groEL promoter, aceA or aceB promoter, etc., and more specifically, may be operably linked to a *Corynebacterium*-originated promoter, lysCP1 promoter (WO2009/096689), or CJ7 promoter (KR Patent No. 0620092 and WO2006/065095) and increase an expression of a polynucleotide encoding the enzyme, but are not limited thereto.

Furthermore, 3) modification of a polynucleotide sequence on chromosome may be performed by inducing modification in a regulatory sequence by deletion, insertion, non-conservative or conservative substitution or a combination there of in a nucleotide sequence, or by replacing with a polynucleotide sequence which is modified to have enhanced activity, in order to enhance activity of the polynucleotide sequence, without being particularly limited thereto.

Further, inactivation of ornithine carbamoyltransfrase (ArgF), glutamate exporter, and acetyl transferase may be performed by methods of inactivating NCgl2523 as previously mentioned:

1) a partial or complete deletion of a polynucleotide encoding the protein;
2) modification of a regulatory sequence to decrease an expression of the polynucleotide;
3) modification of the polynucleotide sequence on chromosome in order to weaken the protein activity; and
4) a combination thereof, without being particularly limited thereto.

Meanwhile, a microorganism of the present invention is a microorganism having putrescine productivity and includes prokaryotic microorganisms expressing proteins including an amino acid represented by SEQ ID NO: 2. Examples of such are *Escherichia* sp., *Shigella* sp., *Citrobacter* sp., *Salmonella* sp., *Enterobacter* sp., *Yersinia* sp., *Klebsiella* sp., *Erwinia* sp., *Corynebacterium* sp., *Brevibacterium* sp., *Lactobacillus* sp., *Selenomanas* sp., *Vibrio* sp., *Pseudomonas* sp., *Streptomyces* sp., *Arcanobacterium* sp., *Alcaligenes* sp. microorganisms, etc. In particular, a microorganism of the present invention may be a microorganism of genus *Corynebacterium*, and more specifically *Corynebacterium glutamicum*, but is not limited thereto.

In one exemplary embodiment, the present invention uses strains having high-concentration putrescine productivity due to an enhanced putrescine biosynthesis pathway from glutamate, which are microorganisms of genus *Corynebacterium* deposited under Accession Nos. KCCM11138P (KR Patent No. 2012-0064046) and KCCM11240P (KR Patent No. 2012-0003634).

In another exemplary embodiment, the present invention uses KCCM11138P and KCCM11240P, which are putrescine-producing strains derived from *Corynebacterium glutamicum* ATCC13032, and DAB12-a (KR Patent No. 2013-0082478) and DAB12-b (KR No. 2013-0082478; DAB12-a ΔNCgl1469), which are putrescine-producing strains derived from *Corynebacterium glutamicum* ATCC13869, each having identical genotypes. ATCC13869 strain may be obtained from American Type Culture Collection (ATCC).

In particular, the present inventors named a microorganism of genus *Corynebacterium* having enhanced putrescine productivity due to inactivation of NCgl2523 activity in *Corynebacterium glutamicum* KCCM11240P, which is a putrescine-producing strain, as *Corynebacterium glutamicum* CC01-0844, and deposited it to Korean Culture Center of Microorganisms (KCCM) under Budapest Treaty as Accession No. KCCM11520P on Feb. 25, 2014.

In another aspect, the present invention provides a method of producing putrescine including:

i) culturing a microorganism of genus *Corynebacterium* having enhanced putrescine productivity wherein a protein having an amino acid sequence represented by SEQ ID NO: 2 is inactivated in a culture medium; and ii) separating putrescine from the cultured microorganism or the culture medium obtained from the above step.

In the method, culturing the microorganism may be performed by known batch culturing methods, continuous culturing methods, fed-batch culturing methods, etc., without being particularly limited thereto. Here, culture conditions may be maintained at optimal pH (e.g., pH 5 to 9, specifically pH 6 to 8, and most specifically pH 6.8) using basic compounds (e.g., sodium hydroxide, potassium hydroxide, or ammonia) or acidic compounds (e.g., phosphoric acid or sulfuric acid), and at an aerobic condition by oxygen or oxygen-containing gas mixture to a cell culture, without being particularly limited thereto. The culture temperature may be maintained at 20° C. to 45° C. and specifically at 25° C. to 40° C., and cultured for about 10 to 160 hours. Putrescine produced by the cultivation may be exported to the culture medium or remain in cells.

Further, the used culture medium may include sugar and carbohydrate (e.g., glucose, sucrose, lactose, fructose, maltose, molasses, starch, and cellulose), oil and fat (e.g., soybean oil, sunflower seed oil, peanut oil, and coconut oil), fatty acid (e.g., palmitic acid, stearic acid, and linoleic acid), alcohol (e.g., glycerol and ethanol), and organic acid (e.g., acetic acid) individually or in combination as a carbon source; nitrogen-containing organic compounds (e.g., peptone, yeast extract, meat juice, malt extract, corn solution, soybean meal powder, and urea), or inorganic compounds (e.g., ammonium sulfate, ammonium chloride, ammonium phosphate, ammonium carbonate, and ammonium nitrate) individually or in combination as a nitrogen source; potassium dihydrogen phosphate, dipotassium phosphate, or sodium-containing salt corresponding thereto individually or in combination as a phosphorus source; and other essential growth-stimulating substances including metal salts (e.g., magnesium sulfate or iron sulfate), amino acids, and vitamins, without being limited thereto.

Separating putrescine produced in the culturing step of the present invention may be performed using a suitable method known in the art depending on culturing methods such as batch, continuous or fed-batch culturing methods, etc., thereby collecting desired amino acids from the culture.

Advantageous Effects

A microorganism of genus *Corynebacterium* having enhanced putrescine productivity of the present invention is modified to inactivate activity of a protein including an amino acid sequence of SEQ ID NO: 2, thereby inducing enhanced activity of a protein which is expected to be a putrescine exporter, specifically NCgl2522, and increasing putrescine export to the outside of cells, and thus may effectively produce putrescine.

DESCRIPTION OF DRAWINGS

FIG. 1 is a schematic diagram showing combined structures of NCgl2523 and the adjacent. In particular, FIG. 1 is a schematic diagram showing a combined structure of NCgl2522-NCgl2523-NCgl2524 which is a combined structure of adjacent genes of a microorganism including NCgl2523 (Type 1); a structure of combined NCgl2522-NCgl2523 and individual NCgl2524 (Type 2); or a combined structure of NCgl2522-NCgl2523 (Type 3).

MODE FOR INVENTION

Hereinafter, the present invention will be described in more detail with reference to Examples. However, the Examples are for illustrative purposes only, and thus the scope of the present invention is not intended to be limited by the Examples.

Example 1

Preparation of NCgl2523-Deleted Strains and Verification of its Putrescine Productivity <1-1> Preparation of NCgl2523-Deleted Strains in ATCC13032-Derived Putrescine-Producing Strains In order to verify whether deletion of NCgl2523 derived from Corynebacterium glutamicum ATCC13032 has an effect in putrescine productivity, vectors for deletion of a gene encoding NCgl2523 were prepared.

In particular, based on the nucleotide sequence of a gene encoding NCgl2523 represented by SEQ ID NO: 1, a pair of primers of SEQ ID NOs: 4 and 5 for obtaining homologous recombination fragments at the N-terminal region of NCgl2523, and a pair of primers of SEQ ID NOs: 6 and 7 for obtaining homologous recombination fragments at the C-terminal region of NCgl2523 were constructed as shown in Table 1.

TABLE 1

| | |
|---|---|
| NCgl2523-del-F1_BamHI (SEQ ID NO: 4) | CGGGATCCATGACTACCTCGCAGC GTTTC |
| NCgl2523-del-R1_SalI (SEQ ID NO: 5) | ACGCGTCGACCTAGTGCGCATTAT TGGCTCC |
| NCgl2523-del-F2 SalI (SEQ ID NO: 6) | ACGCGTCGACAGCCATGCTGGAAA CAATTCTCG |
| NCgl2523-del-R2 XbaI (SEQ ID NO: 7) | CTAGTCTAGAGAGAGCTGCGCATA GTACTG |

PCR was performed using the genomic DNA of Corynebacterium glutamicum ATCC13032 as a template and two pairs of primers, thereby amplifying PCR fragments at the N-terminal and C-terminal regions of NCgl2523 gene. Desired fragments were obtained via electrophoresis of the PCR fragments. Here, PCR reaction was repeated for 30 cycles including 30 seconds of denaturation at 95° C., 30 seconds of annealing at 55° C., and 30 seconds of extension at 72° C. The thus obtained fragments of the N-terminal and C-terminal regions were treated with restriction enzymes BamHI and SalI, and restriction enzymes SalI and XbaI, respectively. The treated fragments were cloned into pDZ vectors treated with restriction enzymes BamHI and XbaI, thereby constructing pDZ-1'NCgl2523(K/O) plasmids.

The pDZ-1'NCgl2523 (K/O) plasmids were each transformed into KCCM11138P (KR Patent No. 10-1348461) and KCCM11240P (KR Patent No. 2013-0082478) by electroporation to obtain transformants. For colony formation, the transformants were plated and cultured on BHIS plate media (Braine heart infusion (37 g/L), sorbitol (91 g/L), and agar (2%)) containing kanamycin (25 µg/mL) and X-gal (5-bromo-4-chloro-3-indolin--D-galactoside). From the formed colonies, blue colonies were selected as strains introduced with pDZ-1'NCgl2523(K/O) plasmids.

The selected strains is cultured in a CM medium (glucose 10 g/L, polypeptone (10 g/L), yeast extract (5 g/L), beef extract (5 g/L), NaCl (2.5 g/L), urea (2 g/L), and pH 6.8) at 30° C. for 8 hours. After serial dilution of each cell culture from $10^{-4}$ to $10^{-10}$, the diluted samples were plated and cultured in an X-gal-containing solid medium to form colonies. From the formed colonies, white colonies, which appeared at a relatively low frequency, were finally selected as strains with deletion of a gene encoding NCgl2523 by a secondary crossover.

PCR was performed using a pair of primers of SEQ ID NOs: 4 and 7 to confirm deletion of a gene encoding NCgl2523 in the finally selected strains. The Corynebacterium glutamicum mutants were each named as KCCM11138P ΔNCgl2523 and KCCM11240P ΔNCgl2523.

<1-2> Preparation of NCgl2523-Deleted Strains in ATCC13869-Derived Putrescine-Producing Strains NCgl2523-deleted strains were constructed from DAB12-a (KR Patent No. 2013-0082478) and DAB12-b (KR Patent No. 2013-0082478; DAB12-a ΔNCgl1469), which are putrescine-producing strains derived from Corynebacterium glutamicum ATCC13869.

In particular, in order to verify a sequence of NCgl2523 gene and the expressed protein therefrom derived from Corynebacterium glutamicum ATCC13869, PCR was performed using genomic DNA of Corynebacterium glutamicum ATCC13869 as a template and a pair of primers of SEQ ID NOs: 4 and 7. Here, PCR reaction was repeated for 30 cycles including 30 seconds of denaturation at 95° C., 30 seconds of annealing at 55° C., and 1 minute 30 seconds of extension at 72° C.

By separating the thus obtained PCR products via electrophoresis and analyzing by sequencing, a gene encoding NCgl2523 derived from Corynebacterium glutamicum ATCC13869 was found to include a nucleotide sequence represented by SEQ ID NO: 3. Further, an amino acid sequence of proteins encoded by the gene was compared to an amino acid sequence of NCgl2523 (SEQ ID NO: 2) derived from Corynebacterium glutamicum ATCC13032, and the result showed 100% homology.

In order to delete a gene encoding NCgl2523 derived from Corynebacterium glutamicum ATCC13869, PCR was performed using genomic DNA of Corynebacterium glutamicum ATCC13869 as a template and two pairs of primers described in Table 1 as in Example <1-1>, and PCR fragments of the N-terminal C-terminal regions of NCgl2523 gene were amplified, thereby obtaining desired fragments via electrophoresis. Here, PCR reaction was repeated for 30 cycles including 30 seconds of denaturation at 95° C., 30 seconds of annealing at 55° C., and 30 seconds of extension at 72° C. The obtained fragments of the N-terminal and C-terminal regions were treated with restriction enzymes BamHI and SalI, and restriction enzymes SalI and XbaI, respectively. The treated fragments were cloned into pDZ vectors treated with restriction enzymes BamHI and XbaI, thereby constructing pDZ-2'NCgl2523(K/O) plasmids.

By transforming pDZ-2'NCgl2523 (K/O) into each of Corynebacterium glutamicum DAB12-a and DAB12-b in the same manner as described in Example <1-1>, strains with deletion of a gene encoding NCgl2523 were selected. The selected Corynebacterium glutamicum mutants were named as DAB12-a ΔNCgl2523 and DAB12-b ΔNCgl2523.

<1-3> Evaluation of Putrescine Productivity of NCgl2523-Deleted Strains

In order to verify the effects of NCgl2523 deletion on putrescine production in putrescine-producing strains, Corynebacterium glutamicum mutants constructed in Example <1-1> and <1-2> were compared for putrescine productivity.

In particular, 4 different types of Corynebacterium glutamicum mutants (KCCM11138P ΔNCgl2523, KCCM11240P ΔNCgl2523, DAB12-a ΔNCgl2523, and DAB12-b ΔNCgl2523) and 4 different types of parent strains (KCCM11138P, KCCM11240P, DAB12-a, and DAB12-b) were each plated on 1 mM arginine-containing CM plate media (1% glucose, 1% polypeptone, 0.5% yeast extract, 0.5% beef extract, 0.25% NaCl, 0.2% urea, 100 μL of 50% NaOH, and 2% agar, at pH 6.8, base on 1 L) and cultured at 30° C. for 24 hours. After inoculating each of the cultured stains using a platinum loop in 25 mL of titer media (8% Glucose, 0.25% soybean proteins, 0.50% corn steep solids, 4% $(NH_4)_2SO_4$, 0.1% $KH_2PO_4$, 0.05% $MgSO_4·7H_2O$, 0.15% urea, 100 g of biotin, 3 mg of thiamine hydrochloride, 3 mg of calcium-pantothenic acid, 3 mg of nicotinamide, and 5% of $CaCO_3$, based on 1 L), shake culturing was carried out at 30° C. and 200 rpm for 98 hours. 1 mM arginine was added to the media for culturing all strains. The concentration of putrescine produced from each culture was measured, and results are shown in Table 2.

TABLE 2

| Strain | Putrescine (g/L) |
| --- | --- |
| KCCM11138P | 9.8 |
| KCCM11138P ΔNCgl2523 | 11.8 |
| KCCM11240P (−) | 12.4 |
| KCCM11240P ΔNCgl2523 | 14.9 |
| DAB12-a | 10.2 |
| DAB12-a ΔNCgl2523 | 12.2 |
| DAB12-b | 13.1 |
| DAB12-b ΔNCgl2523 | 15.2 |

As shown in Table 2, putrescine production was increased in 4 kinds of NCgl2523-deleted Corynebacterium glutamicum mutants.

Example 2

Measurement of Intercellular Putrescine Concentrations in NCgl2523-Deleted Strains To examine changes in intercellular putrescine concentration in Corynebacterium glutamicum mutants having inactivated NCgl2523 activity, intercellular putrescine concentrations were measured in Corynebacterium glutamicum mutant KCCM11240P ΔNCgl2523 and parent strain KCCM11240P by extraction using an organic solvent. Intracellular metabolite analysis was carried out in accordance with a method described in literature (Nakamura J et al., Appl. Environ. Microbiol., 73(14): 4491-4498, 2007).

First, after inoculating each of Corynebacterium glutamicum mutant KCCM11240P ΔNCgl2523 and parent strain KCCM11240P in 25 ml of 1 mM arginine-containing CM liquid media (1% glucose, 1% polypeptone, 0.5% yeast extract, 0.5% beef extract, 0.25% NaCl, 0.2% urea, and 100 μL of 50% NaOH, at pH 6.8, based on 1 L), shake culturing was carried out at 30° C. and 200 rpm. When cell growth reached the exponential phase during cultivation, cells were isolated from the culture media by rapid vacuum filtration (Durapore HV, 0.45 m; Millipore, Billerica, Mass.). The cell-adsorbed filter was washed twice with 10 ml of cooled water and emerged in methanol-containing 5 M morpholine ethanesulfonic acid and 5 M methionine sulfone for 10 minutes. The extraction liquid obtained therefrom was mixed well with an equal volume of chloroform and 0.4-fold volume of water. Only the aqueous phase was applied to a spin column to remove protein contaminants. The filtered extraction liquid was analyzed by capillary electrophoresis mass spectrometry, and the results are shown in Table 3.

TABLE 3

| Strain | Putrescine (mM) |
| --- | --- |
| KCCM11240P | 7 |
| KCCM11240P ΔNCgl2523 | 1 |

As shown in Table 3, the intercellular putrescine concentration was significantly reduced in Corynebacterium glutamicum mutants having inactivated NCgl2523 activity compared to that of parent strain KCCM11240P.

It is suggested that when NCgl2523 is deleted in Corynebacterium glutamicum mutant KCCM11240P, inhibition of NCgl2522 expression is withdrawn and NCgl2522 activity is enhanced, thereby enhancing putrescine-exporting ability and subsequently exporting putrescine produced inside the cell to the outside of cells efficiently.

Example 3

Ortholog Search of NCgl2523 Gene and Gene Context Analysis

Ortholog search was conducted for NCgl2523, which is derived from Corynebacterium glutamicum ATCC13032, using KEGG, MetaCyc Database and NCBI blastP. Via gene cluster, a combined structure of NCgl2523, and NCgl2522 and NCgl2524, which constitute an operon in the genome of each microorganism was examined.

The gene name of NCgl2522 is cgmA, which is a major facilitator superfamily permease belonging to DHA2 family, and the gene name of NCgl2523 is cgmR, which is TetR-family transcriptional regulator. NCgl2524 has not been attributed with a function, but is a major facilitator superfamily permease belonging to UMF1 family.

According to the analysis results, while NCgl2522 and NCgl2523 mostly constitute the same operon, NCgl2524 may be present in the same operons (Type 1), present in a different position in the genome (Type 2), or not present in the genome (Type 3), depending on microorganisms.

In this regard, each of analyzed microorganisms was classified into 3 types according to a combined structure of genes adjacent to NCgl2523. In particular, microorganisms which are expected to have NCgl2523 were classified into a combined structure of NCgl2522-NCgl2523-NCgl2524 (Type 1); a structure of combined NCgl2522-NCgl2523 and individual NCgl2524 (Type 2); or a combined structure of NCgl2522-NCgl2523 (Type 3) (FIG. 1). The classification results are shown in Table 4.

TABLE 4

| Type | Combined structure | Corresponding microorganisms |
|---|---|---|
| | Microorganism having NCgl2523 | Acidovorax avenae, Actinobaculum sp., Actinomyces sp., Actinomyces vaccimaxillae, Actinoplanes missouriensis, Actinosynnema mirum, Agrobacterium tumefaciens, alpha proteobacterium, Amycolatopsis mediterranei, Amycolatopsis orientalis, Arcanobacterium haemolyticum, Arthrobacter aurescens, Arthrobacter sp., Bdellovibrio bacteriovorus, Beutenbergia cavernae, Bordetella bronchiseptica, Bordetella pertussis, Bordetella parapertussis, Brachybacterium paraconglomeratum, Clavibacter michiganensis subsp., Corynebacterium atypicum, Corynebacterium callunae, Corynebacterium casei, Corynebacterium diphtheriae, Corynebacterium glutamicum, Corynebacterium glutamicum AR1, Corynebacterium glutamicum ATCC 13032, Corynebacterium glutamicum ATCC 13869, Corynebacterium glutamicum ATCC 14067, Corynebacterium glutamicum ATCC 21831, Corynebacterium glutamicum K051, Corynebacterium glutamicum MB001, Corynebacterium glutamicum R, Corynebacterium glutamicum SCgG1, Corynebacterium glutamicum SCgG2, Corynebacterium glycinophilum, Corynebacterium maris, Corynebacterium pseudotuberculosis, Corynebacterium sp. ATCC 6931, Corynebacterium terpenotabidum, Corynebacterium ulcerans, Corynebacterium urealyticum, Corynebacterium variabile, Corynebacterium vitaeruminis, Dermabacter sp. HFH0086, Enterobacter cloacae EcWSU1, Enterobacter sp. R4-368, Gammaproteobacteria, Granulicoccus phenolivorans, Hafnia alvei, Ilumatobacter coccineus, Isoptericola variabilis, Janthinobacterium agaricidamnosum, Ketogulonicigenium vulgare, Microbacterium sp., Microbacterium testaceum, Micrococcus luteus, Micromonospora aurantiaca, Micromonospora sp., Mycobacterium gilvum, Nakamurella multipartita, Nesterenkonia alba, Nesterenkonia sp., Nocardia brasiliensis, Nocardia cyriacigeorgica, Nocardia farcinica, Nocardiopsis dassonvillei, Nocardiopsi, kunsanensis, Nocardiopsis sp., Nocardiopsis valliformis, Nocardiopsis xinjiangensis, Ochrobactrum anthropi, Ochrobactrum intermedium, Paracoccus aminophilus, Paracoccus sp. 5503, Pectobacterium carotovorum subsp. carotovorum PCC21, Promicromonospora sukumoe, Propionibacterium acidipropionici, Propionibacterium freudenreichii, Proteobacteria, Providencia stuartii ATCC 33672, Pseudomonas aeruginosa, Pseudomonas cremoricolorata, Pseudomonas geniculata, Pseudomonas stutzeri, pseudonocardia dioxanivorans, Renibacterium salmoninarum, Rhodococcus equi, Rhodococcus erythropolis, Rhodococcus jostii, Rhodococcus opacus B4, Rhodococcus opacus PD630, Rhodococcus pyridinivorans, Saccharomonospora viridis, Saccharopolyspora erythraea, Salinispora, Salinispora arenicola, Salinispora pacifica, Salinispora tropica, Sanguibacter keddieii, Serratia liquefaciens, Serratia marcescens, Serratia plymuthica, Serratia proteamaculans, Serratia sp., Sodalis sp. HS1, Sphingobium chinhatense, Stenotrophomonas maltophilia, Stenotrophomonas sp., Streptococcus anginosus, Streptomyces, Streptomyces alboviridis, Streptomyces albus, Streptomyces atroolivaceus, Streptomyces baarnensis, Streptomyces cyaneofuscatus, Streptomyces fulvissimus, Streptomyces globisporus, Streptomyces griseus, Streptomyces mediolani, Streptomyces scopuliridis, Streptomyces sp., Xanthomonas citri pv. citri, Xenorhabdus nematophila, Yaniella halotolerans, Yersinia enterocolitica |
| 1 | Combined structure of NCgl2522-NCgl2523-NCgl2524 | Corynebacterium callunae, Corynebacterium casei, Corynebacterium glutamicum AR1, Corynebacterium glutamicum ATCC 13032, Corynebacterium glutamicum ATCC 13869, Corynebacterium glutamicum ATCC 14067, Corynebacterium glutamicum ATCC 21831, Corynebacterium glutamicum K051, Corynebacterium glutamicum MB001, Corynebacterium glutamicum R, Corynebacterium glutamicum SCgG1, Corynebacterium glutamicum SCgG2, Corynebacterium vitaeruminis |
| 2 | Structure of combined NCgl2522-NCgl2523; individual NCgl2524 | Actinoplanes missouriensis, Actinosynnema mirum, Amycolatopsis mediterranei, Amycolatopsis mediterranei, Amycolatopsis orientalis, Arcanobacterium haemolyticum, Arthrobacter aurescens, Arthrobacter sp., Bordetella bronchiseptica, Bordetella parapertussis, Bordetella pertussis, Clavibacter michiganensis, Corynebacterium glycinophilum, Corynebacterium maris, Corynebacterium terpenotabidum, Corynebacterium variabile, Isoptericola variabilis, Microbacterium testaceum, Micromonospora aurantiaca, |

TABLE 4-continued

| Type | Combined structure | Corresponding microorganisms |
|---|---|---|
| | | Micromonospora sp. L5, Mycobacterium gilvum, Nakamurella multipartita, Nocardia brasiliensis, Nocardia cyriacigeorgica, Nocardia cyriacigeorgica, Nocardia farcinica, Nocardiopsis dassonvillei, Nocardiopsis dassonvillei, Ochrobactrum anthropi, Paracoccus aminophilus, Propionibacterium acidipropionici, Pseudonocardia dioxanivorans, Renibacterium salmoninarum, Rhodococcus equi, Rhodococcus pyridinivorans, Saccharomonospora viridis, Saccharopolyspora erythraea, Salinispora tropica, Streptomyces albus, Streptomyces fulvissimus, Streptomyces griseus |
| 3 | Combined structure of NCgl2522-NCgl2523 | Acidovorax avenae, Bdellovibrio bacteriovorus, Beutenbergia cavernae, Corynebacterium atypicum, Corynebacterium diphtheriae, Corynebacterium pseudotuberculosis, Corynebacterium ulcerans, Corynebacterium urealyticum, Enterobacter cloacae, Enterobacter sp., Hafnia alvei, Ilumatobacter coccineus, Janthinobacterium agaricidamnosum, Ketogulonicigenium vulgare, Pectobacterium carotovorum subsp. carotovorum PCC21, Providencia stuartii, Pseudomonas aeruginosa, Pseudomonas cremoricolorata, Pseudomonas stutzeri, Sanguibacter keddieii, Serratia liquefaciens, Serratia marcescens, Serratia plymuthica, Serratia proteamaculans, Serratia sp., Sodalis sp. HS1, Stenotrophomonas maltophilia, Xenorhabdus nematophila, Yersinia enterocolitica |

From these results, it is expected that putrescine productivity may be enhanced as in the present invention by inactivating genes encoding NCgl2523 and an amino acid sequence similar thereto, for microorganisms having an amino acid including a sequence similar to NCgl2523 and consisting of an operon with a protein expected to be a putrescine exporter, such as NCgl2522, as in the classification.

Based on the above description, it should be understood by one of ordinary skill in the art that other specific embodiments may be employed in practicing the invention without departing from the technical idea or essential features of the present invention. In this regard, the above-described examples are for illustrative purposes only, and the invention is not intended to be limited by these examples. The scope of the present invention should be understood to include all of the modifications or modified form derived from the meaning and scope of the following claims or its equivalent concepts, rather than the above detailed description.

DEPOSIT DESIGNATION

Depository Authority: Korea Culture Center of Microorganisms
Accession No.: KCCM11520P
Date of Deposit: 20140225

The invention claimed is:

1. An isolated microorganism of genus *Corynebacterium* having putrescine productivity, wherein a protein having an amino acid sequence represented by SEQ ID NO: 2 is inactivated.

2. The microorganism of genus *Corynebacterium* having putrescine productivity according to claim 1, wherein an activity of ornithine decarboxylase (ODC) is further introduced into the microorganism.

3. The microorganism of genus *Corynebacterium* having putrescine productivity according to claim 2, wherein the ODC has an amino acid sequence represented by SEQ ID NO: 10.

4. The microorganism of genus *Corynebacterium* having putrescine productivity according to claim 1, wherein acetyltransferase activity is further inactivated in the microorganism.

5. The microorganism of genus *Corynebacterium* having putrescine productivity according to claim 4, wherein the acetyltransferase comprises an amino acid represented by SEQ ID NO: 15 or 16.

6. The microorganism of genus *Corynebacterium* having putrescine productivity according to claim 1, wherein the microorganism is *Corynebacterium glutamicum*.

7. A method of producing putrescine, comprising:
    culturing a microorganism of genus *Corynebacterium* having putrescine productivity wherein a protein having an amino acid sequence represented by SEQ ID NO: 2 is inactivated, in a culture medium; and
    separating putrescine from the cultured microorganism or the culture medium obtained from the above step.

8. The method of producing putrescine according to claim 7, wherein the microorganism of genus *Corynebacterium* is *Corynebacterium glutamicum*.

* * * * *

SEQUENCE LISTING

<160> NUMBER OF SEQ ID NOS: 16

<210> SEQ ID NO 1
<211> LENGTH: 534
<212> TYPE: DNA
<213> ORGANISM: Corynebacterium glutamicum ATCC13032

<400> SEQUENCE: 1

```
atgcgcacta gtaaaaaaga gatgattctg cgcacggcca tcgattatat cggcgagtac      60
agcctcgaga cgctgagtta cgattcgctc gccgaggcga ccggtctgtc caagtcgggc     120
ttgatttatc atttccccag ccgccatgcg ctgcttttag gcatgcacga gttgcttgcc     180
gacgactggg acaaggaatt gcgcgacata acccgcgacc cagaggatcc acttgagcga     240
ttgcgcgccg tcgtggttac gcttgctgaa aacgtttcgc gccccgagct gcttttgctt     300
atcgacgccc cctcccaccc ggatttcctt aacgcctggc gcactgtaaa tcatcaatgg     360
atccccgaca ccgatgatct ggaaaacgat gcccacaaac gcgccgtcta cctggtgcag     420
ctcgcagccg atggcctctt cgtgcacgat tacattcatg atgatgtcct cagcaagtcc     480
aagcgccaag ccatgctgga aacaattctc gagctgatac caagccagac ttaa           534
```

<210> SEQ ID NO 2

<211> LENGTH: 177
<212> TYPE: PRT
<213> ORGANISM: Corynebacterium glutamicum ATCC13032

<400> SEQUENCE: 2

```
Met Arg Thr Ser Lys Lys Glu Met Ile Leu Arg Thr Ala Ile Asp Tyr
1               5                   10                  15

Ile Gly Glu Tyr Ser Leu Glu Thr Leu Ser Tyr Asp Ser Leu Ala Glu
            20                  25                  30

Ala Thr Gly Leu Ser Lys Ser Gly Leu Ile Tyr His Phe Pro Ser Arg
        35                  40                  45

His Ala Leu Leu Leu Gly Met His Glu Leu Leu Ala Asp Asp Trp Asp
    50                  55                  60

Lys Glu Leu Arg Asp Ile Thr Arg Asp Pro Glu Asp Pro Leu Glu Arg
65                  70                  75                  80

Leu Arg Ala Val Val Val Thr Leu Ala Glu Asn Val Ser Arg Pro Glu
                85                  90                  95

Leu Leu Leu Leu Ile Asp Ala Pro Ser His Pro Asp Phe Leu Asn Ala
            100                 105                 110

Trp Arg Thr Val Asn His Gln Trp Ile Pro Asp Thr Asp Asp Leu Glu
        115                 120                 125

Asn Asp Ala His Lys Arg Ala Val Tyr Leu Val Gln Leu Ala Ala Asp
    130                 135                 140

Gly Leu Phe Val His Asp Tyr Ile His Asp Val Leu Ser Lys Ser
145                 150                 155                 160

Lys Arg Gln Ala Met Leu Glu Thr Ile Leu Glu Leu Ile Pro Ser Gln
                165                 170                 175

Thr
```

<210> SEQ ID NO 3
<211> LENGTH: 534
<212> TYPE: DNA
<213> ORGANISM: Corynebacterium glutamicum ATCC13869

<400> SEQUENCE: 3

```
atgcgcacta gtaaaaaaga gatgattctg cgcacggcca tcgattatat cggcgagtac      60
agcctcgaga cgctgagtta cgattcgctc gccgaggcga ccggtctgtc caagtcgggc     120
ttgatttatc atttccccag ccgccatgcg ctgcttttag gcatgcacga gttgcttgcc     180
gacgactggg acaaggaatt gcgcaacata cccgcgacc cagaggatcc acttgagcga      240
ttgcgcgccg tcgtggttac gcttgctgaa aacgtttcgc gccccgagtt gcttttgctt     300
atcgacgccc cctcccaccc ggatttccta aacgcctggc gcactgtaaa tcatcaatgg     360
atccccgaca ccgatgatct ggaaaacgat gcccacaaac gcgccgtcta cctggtgcag     420
ctcgcagccg atggcctctt cgtgcacgac tacattcatg atgatgtcct cagcaagtcc     480
aagcgccaag ccatgctgga acaattctc gagctgatac cgagccagac ttaa            534
```

<210> SEQ ID NO 4
<211> LENGTH: 29
<212> TYPE: DNA
<213> ORGANISM: Artificial Sequence
<220> FEATURE:
<223> OTHER INFORMATION: NCgl2523-del-F1_BamHI primer

<400> SEQUENCE: 4

```
cgggatccat gactacctcg cagcgtttc                                         29
```

```
<210> SEQ ID NO 5
<211> LENGTH: 31
<212> TYPE: DNA
<213> ORGANISM: Artificial Sequence
<220> FEATURE:
<223> OTHER INFORMATION: NCgl2523-del-R1_SalI primer

<400> SEQUENCE: 5
acgcgtcgac ctagtgcgca ttattggctc c                                31

<210> SEQ ID NO 6
<211> LENGTH: 33
<212> TYPE: DNA
<213> ORGANISM: Artificial Sequence
<220> FEATURE:
<223> OTHER INFORMATION: NCgl2523-del-F2_SalI primer

<400> SEQUENCE: 6
acgcgtcgac agccatgctg gaaacaattc tcg                              33

<210> SEQ ID NO 7
<211> LENGTH: 30
<212> TYPE: DNA
<213> ORGANISM: Artificial Sequence
<220> FEATURE:
<223> OTHER INFORMATION: NCgl2523-del-R2_XbaI primer

<400> SEQUENCE: 7
ctagtctaga gagagctgcg catagtactg                                  30

<210> SEQ ID NO 8
<211> LENGTH: 319
<212> TYPE: PRT
<213> ORGANISM: Corynebacterium glutamicum
<220> FEATURE:
<221> NAME/KEY: MISC_FEATURE
<222> LOCATION: (1)..(319)
<223> OTHER INFORMATION: Ornithine carbamoyl transferase (argF)

<400> SEQUENCE: 8
```

Met Thr Ser Gln Pro Gln Val Arg His Phe Leu Ala Asp Asp Leu
1               5                   10                  15

Thr Pro Ala Glu Gln Ala Glu Val Leu Thr Leu Ala Ala Lys Leu Lys
            20                  25                  30

Ala Ala Pro Phe Ser Glu Arg Pro Leu Glu Gly Pro Lys Ser Val Ala
        35                  40                  45

Val Leu Phe Asp Lys Thr Ser Thr Arg Thr Arg Phe Ser Phe Asp Ala
50                  55                  60

Gly Ile Ala His Leu Gly Gly His Ala Ile Val Val Asp Ser Gly Ser
65                  70                  75                  80

Ser Gln Met Gly Lys Gly Glu Ser Leu Gln Asp Thr Ala Ala Val Leu
                85                  90                  95

Ser Arg Tyr Val Glu Ala Ile Val Trp Arg Thr Tyr Ala His Ser Asn
            100                 105                 110

Phe His Ala Met Ala Glu Thr Ser Thr Val Pro Leu Val Asn Ser Leu
        115                 120                 125

Ser Asp Asp Leu His Pro Cys Gln Ile Leu Ala Asp Leu Gln Thr Ile
    130                 135                 140

Val Glu Asn Leu Ser Pro Glu Glu Gly Pro Ala Gly Leu Lys Gly Lys
145                 150                 155                 160

Lys Ala Val Tyr Leu Gly Asp Gly Asp Asn Asn Met Ala Asn Ser Tyr

```
                165                 170                 175
Met Ile Gly Phe Ala Thr Ala Gly Met Asp Ile Ser Ile Ile Ala Pro
            180                 185                 190

Glu Gly Phe Gln Pro Arg Ala Glu Phe Val Glu Arg Ala Glu Lys Arg
        195                 200                 205

Gly Gln Glu Thr Gly Ala Lys Val Val Thr Asp Ser Leu Asp Glu
    210                 215                 220

Val Ala Gly Ala Asp Val Val Ile Thr Asp Thr Trp Val Ser Met Gly
225                 230                 235                 240

Met Glu Asn Asp Gly Ile Asp Arg Thr Thr Pro Phe Val Pro Tyr Gln
                245                 250                 255

Val Asn Asp Glu Val Met Ala Lys Ala Asn Asp Gly Ala Ile Phe Leu
            260                 265                 270

His Cys Leu Pro Ala Tyr Arg Gly Lys Glu Val Ala Ala Ser Val Ile
        275                 280                 285

Asp Gly Pro Ala Ser Lys Val Phe Asp Glu Ala Glu Asn Arg Leu His
    290                 295                 300

Ala Gln Lys Ala Leu Leu Val Trp Leu Leu Ala Asn Gln Pro Arg
305                 310                 315
```

<210> SEQ ID NO 9
<211> LENGTH: 533
<212> TYPE: PRT
<213> ORGANISM: Corynebacterium glutamicum
<220> FEATURE:
<221> NAME/KEY: MISC_FEATURE
<222> LOCATION: (1)..(533)
<223> OTHER INFORMATION: Glutamate expoter (NCgl1221)

<400> SEQUENCE: 9

```
Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Arg
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Val Ile Pro
            180                 185                 190

Ile Pro Met Leu Gly Ser Glu Asn Ile Thr Asp Val Ile Ala Arg Ser
        195                 200                 205
```

```
Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
                260                 265                 270

Ile Ile Ser Glu Phe Trp Glu Glu Tyr Gly Ser Ala Thr Thr Thr Ser
            275                 280                 285

Gly Thr Leu Ile Asp Ser Leu His Val Glu His Glu Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Val Ile Asn Ala Gly Asn Pro Glu Lys Glu
                340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
    370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
                420                 425                 430

Gly Trp Leu Ser Pro Ser Thr Ala Thr Ser Thr Ala Val Thr Thr Ser
            435                 440                 445

Glu Thr Ser Ala Pro Val Ser Thr Pro Ser Met Thr Val Pro Thr Thr
    450                 455                 460

Val Glu Glu Thr Pro Thr Met Glu Ser Asn Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Glu Thr Thr Ala Ser Gln Thr
                500                 505                 510

Gln Ser Pro Ala Val Glu Ala Pro Thr Ala Val Gln Glu Thr Val Ala
            515                 520                 525

Pro Thr Ser Thr Pro
    530

<210> SEQ ID NO 10
<211> LENGTH: 711
<212> TYPE: PRT
<213> ORGANISM: Unknown
<220> FEATURE:
<223> OTHER INFORMATION: Multispecies proteobacteria ornithine
      decarboxylase (ODC) protein sequence

<400> SEQUENCE: 10

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
```

```
                    20                  25                  30
        Val Ala Ala Val Val Ile Thr Ala Ala Asp Ser Arg Ser Gly Ile Leu
                35                  40                  45
        Ala Leu Leu Lys Arg Thr Gly Phe His Leu Pro Val Phe Leu Tyr Ser
                50                  55                  60
        Glu His Ala Val Glu Leu Pro Ala Gly Val Thr Ala Val Ile Asn Gly
        65                  70                  75                  80
        Asn Glu Gln Gln Trp Leu Glu Leu Glu Ser Ala Ala Cys Gln Tyr Glu
                        85                  90                  95
        Glu Asn Leu Leu Pro Pro Phe Tyr Asp Thr Leu Thr Gln Tyr Val Glu
                    100                 105                 110
        Met Gly Asn Ser Thr Phe Ala Cys Pro Gly His Gln His Gly Ala Phe
                    115                 120                 125
        Phe Lys Lys His Pro Ala Gly Arg His Phe Tyr Asp Phe Phe Gly Glu
                    130                 135                 140
        Asn Val Phe Arg Ala Asp Met Cys Asn Ala Asp Val Lys Leu Gly Asp
        145                 150                 155                 160
        Leu Leu Ile His Glu Gly Ser Ala Lys Asp Ala Gln Lys Phe Ala Ala
                    165                 170                 175
        Lys Val Phe His Ala Asp Lys Thr Tyr Phe Val Leu Asn Gly Thr Ser
                    180                 185                 190
        Ala Ala Asn Lys Val Val Thr Asn Ala Leu Leu Thr Arg Gly Asp Leu
                    195                 200                 205
        Val Leu Phe Asp Arg Asn Asn His Lys Ser Asn His His Gly Ala Leu
                    210                 215                 220
        Ile Gln Ala Gly Ala Thr Pro Val Tyr Leu Glu Ala Ser Arg Asn Pro
        225                 230                 235                 240
        Phe Gly Phe Ile Gly Gly Ile Asp Ala His Cys Phe Asn Glu Glu Tyr
                    245                 250                 255
        Leu Arg Gln Gln Ile Arg Asp Val Ala Pro Glu Lys Ala Asp Leu Pro
                    260                 265                 270
        Arg Pro Tyr Arg Leu Ala Ile Ile Gln Leu Gly Thr Tyr Asp Gly Thr
                    275                 280                 285
        Val Tyr Asn Ala Arg Gln Val Ile Asp Thr Val Gly His Leu Cys Asp
                    290                 295                 300
        Tyr Ile Leu Phe Asp Ser Ala Trp Val Gly Tyr Glu Gln Phe Ile Pro
        305                 310                 315                 320
        Met Met Ala Asp Ser Ser Pro Leu Leu Leu Glu Leu Asn Glu Asn Asp
                    325                 330                 335
        Pro Gly Ile Phe Val Thr Gln Ser Val His Lys Gln Gln Ala Gly Phe
                    340                 345                 350
        Ser Gln Thr Ser Gln Ile His Lys Lys Asp Asn His Ile Arg Gly Gln
                    355                 360                 365
        Ala Arg Phe Cys Pro His Lys Arg Leu Asn Asn Ala Phe Met Leu His
                    370                 375                 380
        Ala Ser Thr Ser Pro Phe Tyr Pro Leu Phe Ala Ala Leu Asp Val Asn
        385                 390                 395                 400
        Ala Lys Ile His Glu Gly Glu Ser Gly Arg Arg Leu Trp Ala Glu Cys
                    405                 410                 415
        Val Glu Ile Gly Ile Glu Ala Arg Lys Ala Ile Leu Ala Arg Cys Lys
                    420                 425                 430
        Leu Phe Arg Pro Phe Ile Pro Pro Val Val Asp Gly Lys Leu Trp Gln
                    435                 440                 445
```

```
Asp Tyr Pro Thr Ser Val Leu Ala Ser Asp Arg Arg Phe Ser Phe
    450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
                500                 505                 510

Ala His Tyr Leu Arg Glu Asn Gly Ile Val Pro Glu Lys Cys Asp Leu
            515                 520                 525

Asn Ser Ile Leu Phe Leu Thr Pro Ala Glu Ser His Glu Lys Leu
530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
                580                 585                 590

Asp Leu Tyr Val Ser Phe Asp Val Lys Asp Leu Gln Lys Ala Met Phe
            595                 600                 605

Arg Gln Gln Ser Phe Pro Ser Val Val Met Asn Pro Gln Asp Ala His
    610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
                660                 665                 670

Phe Leu Ala Leu Glu Glu Gly Val Asn Leu Leu Pro Gly Phe Ser Pro
            675                 680                 685

Glu Leu Gln Gly Val Tyr Ser Glu Thr Asp Ala Asp Gly Val Lys Arg
    690                 695                 700

Leu Tyr Gly Tyr Val Leu Lys
705                 710

<210> SEQ ID NO 11
<211> LENGTH: 357
<212> TYPE: PRT
<213> ORGANISM: Corynebacterium glutamicum
<220> FEATURE:
<221> NAME/KEY: MISC_FEATURE
<222> LOCATION: (1)..(357)
<223> OTHER INFORMATION: Acetyl gamma glutamyl phosphate reductase
      (ArgC)

<400> SEQUENCE: 11

Met Ile Met His Asn Val Tyr Gly Val Thr Met Thr Ile Lys Val Ala
1               5                   10                  15

Ile Ala Gly Ala Ser Gly Tyr Ala Gly Gly Glu Ile Leu Arg Leu Leu
            20                  25                  30

Leu Gly His Pro Ala Tyr Ala Ser Gly Glu Leu Glu Ile Gly Ala Leu
        35                  40                  45

Thr Ala Ala Ser Thr Ala Gly Ser Thr Leu Gly Glu Leu Met Pro His
    50                  55                  60

Ile Pro Gln Leu Ala Asp Arg Val Ile Gln Asp Thr Thr Ala Glu Thr
65                  70                  75                  80
```

```
Leu Ala Gly His Asp Val Val Phe Leu Gly Leu Pro His Gly Phe Ser
                85                  90                  95

Ala Glu Ile Ala Leu Gln Leu Gly Pro Asp Val Thr Val Ile Asp Cys
            100                 105                 110

Ala Ala Asp Phe Arg Leu Gln Asn Ala Ala Asp Trp Glu Lys Phe Tyr
        115                 120                 125

Gly Ser Glu His Gln Gly Thr Trp Pro Tyr Gly Ile Pro Glu Met Pro
    130                 135                 140

Gly His Arg Glu Ala Leu Arg Gly Ala Lys Arg Val Ala Val Pro Gly
145                 150                 155                 160

Cys Phe Pro Thr Gly Ala Thr Leu Ala Leu Leu Pro Ala Val Gln Ala
                165                 170                 175

Gly Leu Ile Glu Pro Asp Val Ser Val Val Ser Ile Thr Gly Val Ser
            180                 185                 190

Gly Ala Gly Lys Lys Ala Ser Val Ala Leu Leu Gly Ser Glu Thr Met
        195                 200                 205

Gly Ser Leu Lys Ala Tyr Asn Thr Ser Gly Lys His Arg His Thr Pro
    210                 215                 220

Glu Ile Ala Gln Asn Leu Gly Glu Val Ser Asp Lys Pro Val Lys Val
225                 230                 235                 240

Ser Phe Thr Pro Val Leu Ala Pro Leu Pro Arg Gly Ile Leu Thr Thr
                245                 250                 255

Ala Thr Ala Pro Leu Lys Glu Gly Val Thr Ala Glu Gln Ala Arg Ala
            260                 265                 270

Val Tyr Glu Glu Phe Tyr Ala Gln Glu Thr Phe Val His Val Leu Pro
        275                 280                 285

Glu Gly Ala Gln Pro Gln Thr Gln Ala Val Leu Gly Ser Asn Met Cys
    290                 295                 300

His Val Gln Val Glu Ile Asp Glu Glu Ala Gly Lys Val Leu Val Thr
305                 310                 315                 320

Ser Ala Ile Asp Asn Leu Thr Lys Gly Thr Ala Gly Ala Ala Val Gln
                325                 330                 335

Cys Met Asn Leu Ser Val Gly Phe Asp Glu Ala Ala Gly Leu Pro Gln
            340                 345                 350

Val Gly Val Ala Pro
        355

<210> SEQ ID NO 12
<211> LENGTH: 388
<212> TYPE: PRT
<213> ORGANISM: Corynebacterium glutamicum
<220> FEATURE:
<221> NAME/KEY: MISC_FEATURE
<222> LOCATION: (1)..(388)
<223> OTHER INFORMATION: Acetyl glutamate synthase or Ornithine acetyl
      transferase (ArgJ)

<400> SEQUENCE: 12

Met Ala Glu Lys Gly Ile Thr Ala Pro Lys Gly Phe Val Ala Ser Ala
1               5                   10                  15

Thr Thr Ala Gly Ile Lys Ala Ser Gly Asn Pro Asp Met Ala Leu Val
            20                  25                  30

Val Asn Gln Gly Pro Glu Phe Ser Ala Ala Val Phe Thr Arg Asn
        35                  40                  45

Arg Val Phe Ala Ala Pro Val Lys Val Ser Arg Glu Asn Val Ala Asp
    50                  55                  60
```

Gly Gln Ile Arg Ala Val Leu Tyr Asn Ala Gly Asn Ala Asn Ala Cys
65                  70                  75                  80

Asn Gly Leu Gln Gly Glu Lys Asp Ala Arg Glu Ser Val Ser His Leu
            85                  90                  95

Ala Gln Asn Leu Gly Leu Glu Asp Ser Asp Ile Gly Val Cys Ser Thr
            100                 105                 110

Gly Leu Ile Gly Glu Leu Leu Pro Met Asp Lys Leu Asn Ala Gly Ile
            115                 120                 125

Asp Gln Leu Thr Ala Glu Gly Ala Leu Gly Asp Asn Gly Ala Ala Ala
            130                 135                 140

Ala Lys Ala Ile Met Thr Thr Asp Thr Val Asp Lys Glu Thr Val Val
145                 150                 155                 160

Phe Ala Asp Gly Trp Thr Val Gly Gly Met Gly Lys Gly Val Gly Met
            165                 170                 175

Met Ala Pro Ser Leu Ala Thr Met Leu Val Cys Leu Thr Thr Asp Ala
            180                 185                 190

Ser Val Thr Gln Glu Met Ala Gln Ile Ala Leu Ala Asn Ala Thr Ala
            195                 200                 205

Val Thr Phe Asp Thr Leu Asp Ile Asp Gly Ser Thr Ser Thr Asn Asp
            210                 215                 220

Thr Val Phe Leu Leu Ala Ser Gly Ala Ser Gly Ile Thr Pro Thr Gln
225                 230                 235                 240

Asp Glu Leu Asn Asp Ala Val Tyr Ala Ala Cys Ser Asp Ile Ala Ala
            245                 250                 255

Lys Leu Gln Ala Asp Ala Glu Gly Val Thr Lys Arg Val Ala Val Thr
            260                 265                 270

Val Val Gly Thr Thr Asn Asn Glu Gln Ala Ile Asn Ala Ala Arg Thr
            275                 280                 285

Val Ala Arg Asp Asn Leu Phe Lys Cys Ala Met Phe Gly Ser Asp Pro
            290                 295                 300

Asn Trp Gly Arg Val Leu Ala Ala Val Gly Met Ala Asp Ala Asp Met
305                 310                 315                 320

Glu Pro Glu Lys Ile Ser Val Phe Phe Asn Gly Gln Ala Val Cys Leu
            325                 330                 335

Asp Ser Thr Gly Ala Pro Gly Ala Arg Glu Val Asp Leu Ser Gly Ala
            340                 345                 350

Asp Ile Asp Val Arg Ile Asp Leu Gly Thr Ser Gly Glu Gly Gln Ala
            355                 360                 365

Thr Val Arg Thr Thr Asp Leu Ser Phe Ser Tyr Val Glu Ile Asn Ser
            370                 375                 380

Ala Tyr Ser Ser
385

<210> SEQ ID NO 13
<211> LENGTH: 317
<212> TYPE: PRT
<213> ORGANISM: Corynebacterium sp.
<220> FEATURE:
<221> NAME/KEY: MISC_FEATURE
<222> LOCATION: (1)..(317)
<223> OTHER INFORMATION: Acetyl glutamate kinase (ArgB)

<400> SEQUENCE: 13

Met Asn Asp Leu Ile Lys Asp Leu Gly Ser Glu Val Arg Ala Asn Val
1               5                   10                  15

```
Leu Ala Glu Ala Leu Pro Trp Leu Gln His Phe Arg Asp Lys Ile Val
            20                  25                  30

Val Val Lys Tyr Gly Gly Asn Ala Met Val Asp Asp Leu Lys Ala
        35                  40                  45

Ala Phe Ala Ala Asp Met Val Phe Leu Arg Thr Val Gly Ala Lys Pro
 50                  55                  60

Val Val Val His Gly Gly Pro Gln Ile Ser Glu Met Leu Asn Arg
 65              70                  75                  80

Val Gly Leu Gln Gly Glu Phe Lys Gly Gly Phe Arg Val Thr Thr Pro
                85                  90                  95

Glu Val Met Asp Ile Val Arg Met Val Leu Phe Gly Gln Val Gly Arg
            100                 105                 110

Asp Leu Val Gly Leu Ile Asn Ser His Gly Pro Tyr Ala Val Gly Thr
            115                 120                 125

Ser Gly Glu Asp Ala Gly Leu Phe Thr Ala Gln Lys Arg Met Val Asn
        130                 135                 140

Ile Asp Gly Val Pro Thr Asp Ile Gly Leu Val Gly Asp Ile Ile Asn
145                 150                 155                 160

Val Asp Ala Ser Ser Leu Met Asp Ile Ile Glu Ala Gly Arg Ile Pro
            165                 170                 175

Val Val Ser Thr Ile Ala Pro Gly Glu Asp Gly Gln Ile Tyr Asn Ile
            180                 185                 190

Asn Ala Asp Thr Ala Ala Gly Ala Leu Ala Ala Ile Gly Ala Glu
        195                 200                 205

Arg Leu Leu Val Leu Thr Asn Val Glu Gly Leu Tyr Thr Asp Trp Pro
    210                 215                 220

Asp Lys Ser Ser Leu Val Ser Lys Ile Lys Ala Thr Glu Leu Glu Ala
225                 230                 235                 240

Ile Leu Pro Gly Leu Asp Ser Gly Met Ile Pro Lys Met Glu Ser Cys
                245                 250                 255

Leu Asn Ala Val Arg Gly Gly Val Ser Ala Ala His Val Ile Asp Gly
            260                 265                 270

Arg Ile Ala His Ser Val Leu Leu Glu Leu Thr Met Gly Gly Ile
    275                 280                 285

Gly Thr Met Val Leu Pro Asp Val Phe Asp Arg Glu Asn Tyr Pro Glu
290                 295                 300

Gly Thr Val Phe Arg Lys Asp Asp Lys Asp Gly Glu Leu
305                 310                 315

<210> SEQ ID NO 14
<211> LENGTH: 391
<212> TYPE: PRT
<213> ORGANISM: Corynebacterium glutamicum
<220> FEATURE:
<221> NAME/KEY: MISC_FEATURE
<222> LOCATION: (1)..(391)
<223> OTHER INFORMATION: Acetyl ornithine aminotransferase (ArgD)

<400> SEQUENCE: 14

Met Ser Thr Leu Glu Thr Trp Pro Gln Val Ile Ile Asn Thr Tyr Gly
1               5                   10                  15

Thr Pro Pro Val Glu Leu Val Ser Gly Lys Gly Ala Thr Val Thr Asp
            20                  25                  30

Asp Gln Gly Asn Val Tyr Ile Asp Leu Leu Ala Gly Ile Ala Val Asn
        35                  40                  45

Ala Leu Gly His Ala His Pro Ala Ile Ile Glu Ala Val Thr Asn Gln
```

```
Ile Gly Gln Leu Gly His Val Ser Asn Leu Phe Ala Ser Arg Pro Val
65                  70                  75                  80

Val Glu Val Ala Glu Glu Leu Ile Lys Arg Phe Ser Leu Asp Asp Ala
                85                  90                  95

Thr Leu Ala Ala Gln Thr Arg Val Phe Phe Cys Asn Ser Gly Ala Glu
            100                 105                 110

Ala Asn Glu Ala Ala Phe Lys Ile Ala Arg Leu Thr Gly Arg Ser Arg
        115                 120                 125

Ile Leu Ala Ala Val His Gly Phe His Gly Arg Thr Met Gly Ser Leu
    130                 135                 140

Ala Leu Thr Gly Gln Pro Asp Lys Arg Glu Ala Phe Leu Pro Met Pro
145                 150                 155                 160

Ser Gly Val Glu Phe Tyr Pro Tyr Gly Asp Thr Asp Tyr Leu Arg Lys
                165                 170                 175

Met Val Glu Thr Asn Pro Thr Asp Val Ala Ala Ile Phe Leu Glu Pro
            180                 185                 190

Ile Gln Gly Glu Thr Gly Val Val Pro Ala Pro Glu Gly Phe Leu Lys
        195                 200                 205

Ala Val Arg Glu Leu Cys Asp Glu Tyr Gly Ile Leu Met Ile Thr Asp
    210                 215                 220

Glu Val Gln Thr Gly Val Gly Arg Thr Gly Asp Phe Phe Ala His Gln
225                 230                 235                 240

His Asp Gly Val Val Pro Asp Val Val Thr Met Ala Lys Gly Leu Gly
                245                 250                 255

Gly Gly Leu Pro Ile Gly Ala Cys Leu Ala Thr Gly Arg Ala Ala Glu
            260                 265                 270

Leu Met Thr Pro Gly Lys His Gly Thr Thr Phe Gly Gly Asn Pro Val
        275                 280                 285

Ala Cys Ala Ala Ala Lys Ala Val Leu Ser Val Val Asp Asp Ala Phe
    290                 295                 300

Cys Ala Glu Val Ala Arg Lys Gly Glu Leu Phe Lys Glu Leu Leu Ala
305                 310                 315                 320

Lys Val Asp Gly Val Val Asp Val Arg Gly Arg Gly Leu Met Leu Gly
                325                 330                 335

Val Val Leu Glu Arg Asp Val Ala Lys Gln Ala Val Leu Asp Gly Phe
            340                 345                 350

Lys His Gly Val Ile Leu Asn Ala Pro Ala Asp Asn Ile Ile Arg Leu
        355                 360                 365

Thr Pro Pro Leu Val Ile Thr Asp Glu Glu Ile Ala Asp Ala Val Lys
    370                 375                 380

Ala Ile Ala Glu Thr Ile Ala
385                 390

<210> SEQ ID NO 15
<211> LENGTH: 203
<212> TYPE: PRT
<213> ORGANISM: Corynebacterium glutamicum ATCC13032

<400> SEQUENCE: 15

Met Ser Pro Thr Val Leu Pro Ala Thr Gln Ala Asp Phe Pro Lys Ile
1               5                   10                  15

Val Asp Val Leu Val Glu Ala Phe Ala Asn Asp Pro Ala Phe Leu Arg
            20                  25                  30
```

```
Trp Ile Pro Gln Pro Asp Pro Gly Ser Ala Lys Leu Arg Ala Leu Phe
            35                  40                  45

Glu Leu Gln Ile Glu Lys Gln Tyr Ala Val Ala Gly Asn Ile Asp Val
 50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Met Leu Pro Arg
                85                  90                  95

Leu Val Ser Ile Phe Gly Ile Lys Ala Ala Gln Val Ala Trp Thr Asp
                100                 105                 110

Leu Ser Ser Ala Arg Phe His Pro Lys Phe Pro His Trp Tyr Leu Tyr
                115                 120                 125

Thr Val Ala Thr Ser Ser Ala Arg Gly Thr Gly Val Gly Ser Ala
            130                 135                 140

Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
                165                 170                 175

Val Pro Leu Gly Tyr Ile Pro Ser Asp Asp Gly Thr Pro Glu Leu
            180                 185                 190

Ala Met Trp Lys Pro Pro Ala Met Pro Thr Val
            195                 200

<210> SEQ ID NO 16
<211> LENGTH: 203
<212> TYPE: PRT
<213> ORGANISM: Corynebacterium glutamicum ATCC13869

<400> SEQUENCE: 16

Met Ser Pro Thr Val Leu Pro Ala Thr Gln Ala Asp Phe Pro Lys Ile
1               5                   10                  15

Val Asp Val Leu Val Glu Ala Phe Ala Asn Asp Pro Ala Phe Leu Arg
            20                  25                  30

Trp Ile Pro Gln Pro Asp Pro Gly Ser Ala Lys Leu Arg Ala Leu Phe
            35                  40                  45

Glu Leu Gln Ile Glu Lys Gln Tyr Ala Val Ala Gly Asn Ile Asp Val
 50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Ile Leu Pro Arg
                85                  90                  95

Leu Val Ser Ile Phe Gly Ile Lys Ala Ala Gln Val Ala Trp Thr Asp
                100                 105                 110

Leu Ser Ser Ala Arg Phe His Pro Lys Phe Pro His Trp Tyr Leu Tyr
                115                 120                 125

Thr Val Ala Thr Ser Ser Ala Arg Gly Thr Gly Val Gly Ser Ala
            130                 135                 140

Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
                165                 170                 175
```

-continued

```
Val Pro Leu Gly Tyr Ile Pro Ser Asp Asp Asp Gly Thr Pro Glu Leu
            180                 185                 190

Ala Met Trp Lys Pro Pro Ala Met Pro Thr Val
        195                 200
```